United States Patent [19]

Mesa

[11] Patent Number: 4,678,461
[45] Date of Patent: Jul. 7, 1987

[54] AUTOMATIC INJECTOR WITH IMPROVED GLASS CONTAINER PROTECTOR

[75] Inventor: Clarence M. Mesa, Rockville, Md.

[73] Assignee: Survival Technology, Inc., Bethesda, Md.

[21] Appl. No.: 667,443

[22] Filed: Nov. 1, 1984

[51] Int. Cl.$^4$ .............................................. A61M 5/20
[52] U.S. Cl. ..................................... 604/157; 604/225
[58] Field of Search ............... 604/225, 223, 187, 156, 604/157

[56] References Cited

U.S. PATENT DOCUMENTS

| | | |
|---|---|---|
| 2,832,339 | 4/1958 | Sarnoff et al. . |
| 3,380,449 | 4/1968 | Sarnoff . |
| 3,391,695 | 7/1968 | Sarnoff . |
| 3,424,155 | 1/1969 | Sarnoff . |
| 3,712,301 | 1/1973 | Sarnoff . |
| 3,797,489 | 3/1974 | Sarnoff . |
| 3,882,863 | 5/1975 | Sarnoff et al. . |
| 4,014,331 | 3/1977 | Head ................................... 604/223 |
| 4,031,893 | 6/1977 | Kaplan et al. . |
| 4,226,235 | 10/1980 | Sarnoff et al. . |
| 4,329,988 | 5/1982 | Sarnoff et al. . |

Primary Examiner—John D. Yasko
Attorney, Agent, or Firm—Cushman, Darby & Cushman

[57] ABSTRACT

An automatic injector having a glass container protecting sleeve of thin plastic material assembled in an operative position within the injector housing with respect to the glass medicament container when the stressed spring actuating assembly is in an unreleased condition so as to protect the glass container against fracture (1) due to handling impacts prior to release of the stressed spring assembly and (2) due to the force transmitted to the plunger following the release of the stressed assembly. The sleeve includes a cylindrical portion disposed in engagement with a cylindrical periphery of the glass container when the protective sleeve is in its operative position and an annular flange extending from the rear end of the cylindrical portion disposed in rearwardly adjacent relation to the rear end edge of the glass container when the protective sleeve is in its operative position.

6 Claims, 4 Drawing Figures

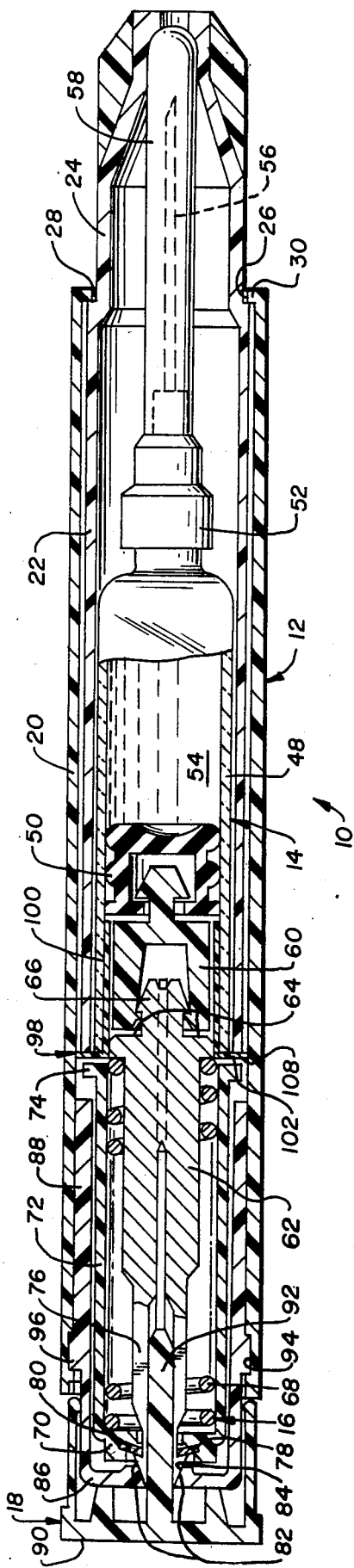
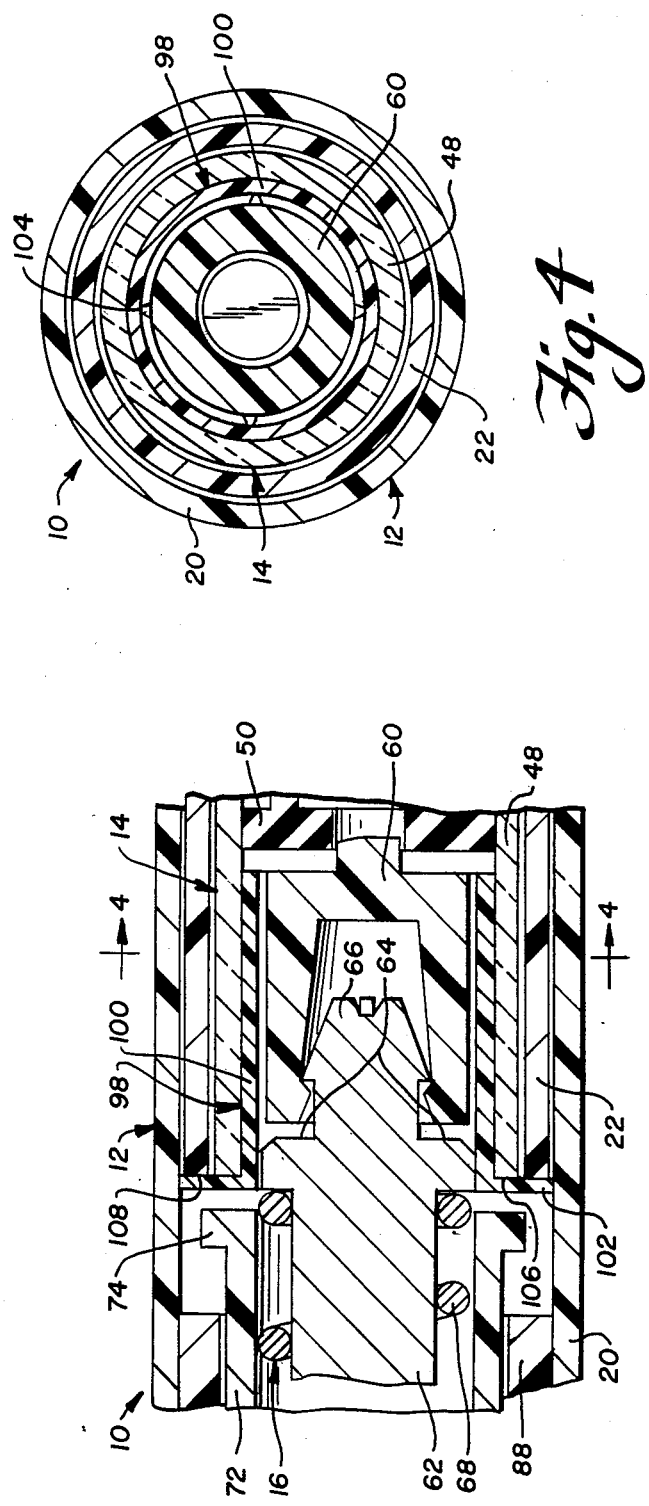
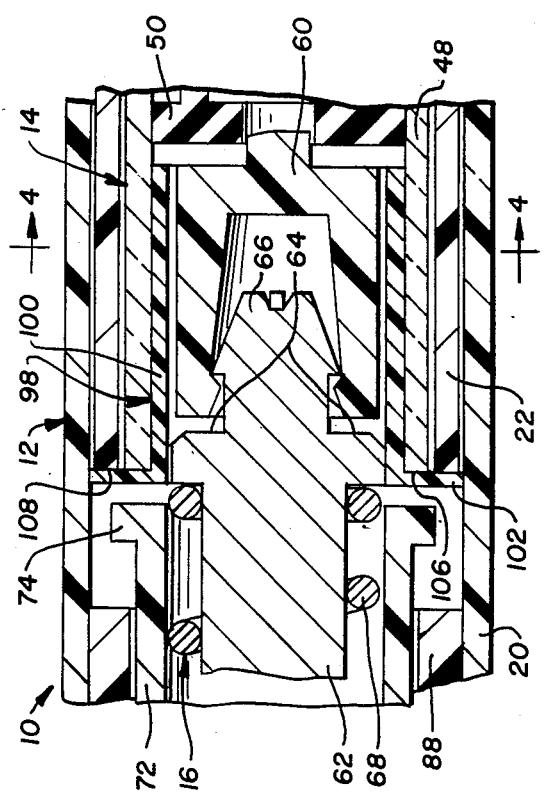

AUTOMATIC INJECTOR WITH IMPROVED GLASS CONTAINER PROTECTOR

This invention relates to automatic injectors and, more particularly, to improvements for protecting the glass medicament containers in such injectors from breakage.

The type of automatic injector which is herein contemplated is exemplified in the disclosure of U.S. Pat. No. 4,031,893. See also U.S. Pat. Nos. 3,882,863; 3,797,489; and 3,712,301.

The injector consists essentially of a housing assembly, a medicament cartridge injecting assembly and a stressed spring assembly having a manually operable safety assembly. The medicament injecting assembly includes a medicament container which is made of glass in the form of a cylindrical wall which is necked in at one end and formed with a rear end structure at the opposite end. The necked in end is connected through a hub assembly to a hypodermic needle, and preferably the hub assembly includes a burstable diaphragm which maintains the medicament dosage within the container sealed with respect to the metal which forms the needle. The rear end of the medicament dosage is sealed within the container by a resilient plunger. Preferably, the plunger is spaced forwardly from the rear edge of the glass container and a spacer serves to connect the plunger with the stressed spring assembly when all of the sub-assemblies are assembled. The glass container is mounted within the housing so as to be movable forwardly during the initial power stroke of the stressed spring assembly when the latter is released. During the forward movement of the container, the needle is extended into the muscle tissue of the user. Thereafter, the medicament dosage is discharged from the container through the needle into the muscle tissue of the user.

Because the container is mounted for movement within the housing, it sometimes occurs when the automatic injector is accidentally dropped that there is sufficient relative movement between the glass container and the rigid or metal structures adjacent thereto to cause a hairline fracture or an actual breakage of the glass. In addition, in the event that the components of the stressed spring assembly are not properly aligned with the medicament injecting assembly when the injector is assembled, release of the stressed spring assembly can result in glass breakage by an impact imparted to the glass from a portion of the collet or of the volutes of the coil spring.

It will be understood that glass breakage even in the nature of a hairline fracture which occurs as a result of droppage at a time before use is to be made of the injector can result in the leakage of the medicament from the container or contamination thereof as well as a complete fracturing of the glass during use, with a resultant failure to effect full injection into the user. Similarly, fracture of the glass by contact with the movable metal parts which move adjacent thereto during the release of the stressed spring assembly can result in complete fracture of the glass container and hence failure to inject the medicament dosage into the user.

Heretofore, one procedure for minimizing the likelihood of glass breakage in the manner indicated above was to heat temper the glass. Such procedures all but eliminated operational breakage and materially reduced droppage breakage to the most severe cases. Heat tempering, however, adds substantial cost to the injector.

An object of the present invention is to provide an automatic injector of the type described with an improved means for protecting the glass container of the injector against fracture due to droppage and improper operation which is as effective as heat treating but less expensive. In accordance with the principles of the present invention this objective is accomplished by utilizing as the improved protecting means a sleeve of thin plastic material assembled in an operative position within the housing with respect to the glass container when the stressed spring actuating assembly is in an unreleased condition so as to protect the glass container against fracture (1) due to handling impacts prior to release of the stressed spring assembly and (2) due to the force transmitted to the plunger following the release of the stressed assembly. The sleeve includes a cylindrical portion disposed in engagement with a cylindrical periphery of the glass container when the protective sleeve is in its operative position and an annular flange extending from the rear end of the cylindrical portion disposed in rearwardly adjacent relation to the rear end edge of the glass container when the protective sleeve is in its operative position.

Preferably, the plunger is slidably sealingly mounted within the interior periphery of the container at a position forwardly of the rear end edge thereof when the stressed spring actuating assembly is in its unreleased condition so that the cylindrical portion of the sleeve extends forwardly from the inner periphery of the annular flange in engagement with the portion of the cylindrical interior periphery of the container extending from the rear end edge thereof to the position forwardly therefrom within which the plunger is mounted.

Preferably, the housing includes a fixed outer tubular member including a rear end edge normally disposed in contiguous surrounding relation with the rear end edge of the container so that the sleeve flange extends radially outwardly beyond the rear end edge of the container in rearwardly adjacent relation to the rear end edge of the inner tubular housing member so as to be held against forward movement by engagement therewith so that the cylindrical portion thereof will act as a centering stationary guide for the stressed spring assembly when the latter is released to move the plunger as aforesaid.

These and other objects of the present invention will become more apparent during the course of the following detailed description and appended claims.

The invention may best be understood with reference to the accompanying drawings, wherein an illustrative embodiment is shown.

In the drawings:

FIG. 1 is a longitudinal sectional view of an automatic injector embodying the principles of the present invention, showing the same in its inoperative storage position;

FIG. 3 is an enlarged fragmentary view similar to FIG. 1 illustrating on a larger scale the protective sleeve improvement embodying the principles of the present invention; and FIG. 4 is a cross-sectional view taken along along the line 4—4 of FIG. 3.

Figure 2:
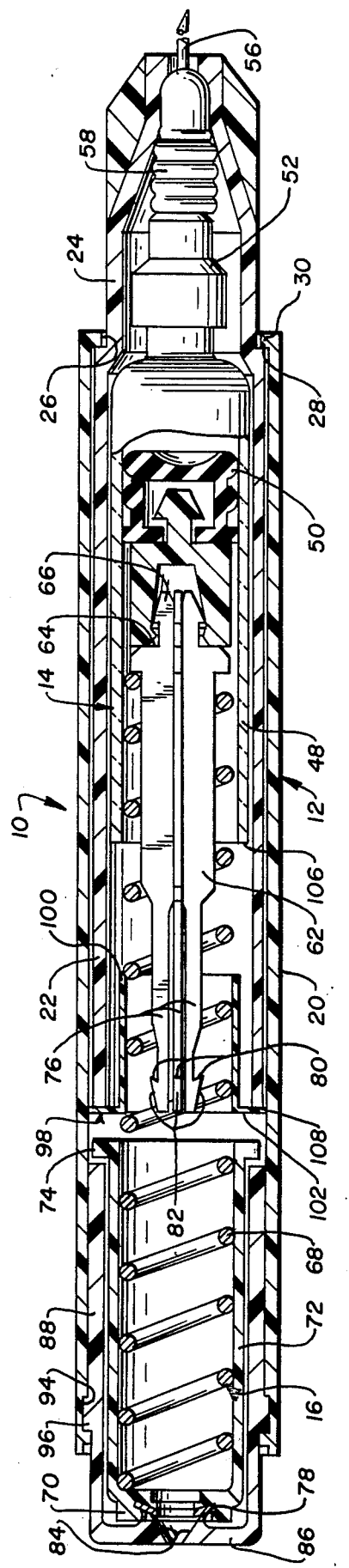
FIG. 2 is a view similar to FIG. 1, showing the position of the parts of the injector after operation.

Referring now more particularly to the drawings there is shown therein an automatic injector assembly, generally indicated at 10, which embodies the improvements constructed in accordance with the principles of the present invention. The injector assembly 10 includes, in general, a housing assembly, generally indicated at 12, a medicament injecting assembly, generally indicated at 14, mounted within the forward end portion of the housing assembly, and a stressed spring assembly, generally indicated at 16, within the rearward end portion of the housing assembly 12, disposed in operating relation to the latter. Mounted on the rearward end portion of the housing structure 12 is a manually operable safety assembly, generally indicated at 18, operatively associated with the stressed spring assembly 16.

The housing assembly 12 includes an outer cylindrical tubular housing member 20 and a cooperating inner cylindrical tubular housing member 22 within which the medicament injecting assembly 14 is mounted. As best shown in FIG. 1, the housing member 22 includes a forward end portion 24 of reduced diameter which extends forwardly through a forward opening 26 in the cooperating outer housing member 20 and constitutes a forward end of the housing assembly 12 which is adapted to engage the patient.

The reduced forward end portion 24 of the housing member 22 defines a forwardly facing annular shoulder 28 which abuts against the rearward suface of an annular flange 30 formed interiorly within the outer housing member 20 in the forward end thereof so as to also define the opening 26. Flange 30 thus positively prevents forward movement of the housing member 22 within the housing member 20 while permitting the latter to be moved forwardly with respect to the housing member 22 when the forward end thereof is in engagement with a patient.

As best shown in FIG. 1, the medicament injecting assembly 14 includes a cylindrical container 48 of glass, the rearward end of which is open and has a plunger 50 slidably mounted therein. The forward end of the container 48 is necked down and flanged to fixably receive a hub 52. Hub 52 is preferably constructed in accordance with the teachings contained in U.S Pat. No. 3,380,449 (see also U.S. Pat. Nos. 3,391,695 and 3,424,155) so as to contain a burstable diaphragm (not shown) which serves to seal a liquid medicament dosage 54 within the container forwardly of the plunger 50 from normal contact with a hypodermic needle 56 fixedly supported by the hub 52 and extending forwardly therefrom. A rubber sheath 58 encompasses the exterior of the needle 56 so as to maintain the same in a sterile condition. As shown, a spacer 60 is connected with the plunger 50 so as to axially fill the rearward end of the container. In this regard see U.S. Pat. No. 4,031,893, the disclosure of which is hereby incorporated by reference into the present specification, together with the disclosures of U.S. Pat. Nos. 2,832,339, 3,380,449, 3,391,695, 3,424,155, 3,712,301, 3,797,489, 3,882,863, 4,226,235 and 4,329,988 previously discussed.

The stressed spring assembly 16 includes an inner collet member 62 made up of two interfitted stampings providing shoulders 64 on the forward ends thereof for engaging the rearward surface of the spacer 60. Spacer connecting barbs 66 extend forwardly from the collet member 62 in connected relation with the spacer 60. A coil spring 68 is disposed around the inner member 62 and its forward end engages the rearward surface of the shoulders 64. The spring 68 is placed under stress by compressing the rearward end of the spring 68 in engagement with the forward surface of an apertured rear wall 70 of a tubular member 72. The tubular member 72 extends forwardly in surrounding relation to the exterior of the compressed coil spring 68, and has its forward extremity exteriorly flanged, as indicated at 74, to confront or engage the rear end of housing member 22.

The rearward end portions of the stampings of the collet member 62 are tapered rearwardly and split to define four releasable spring fingers 76 which extend through the central aperture in the rear wall 70 and through an apertured locking ring 78 carried on the rearward surface of the rear wall 70. Spring fingers 76 include forwardly facing locking surfaces 80 engagable with the locking ring 78 and rearwardly and outwardly facing cam release surfaces 82. Cam surfaces 82 are adapted to engage a mating forwardly and inwardly facing frustoconical cam release surface 84 formed on the interior of an aperture rear wall 86 of an outer cylindrical housing member 88 slidably surrounding the exterior periphery of the cylindrical member 72.

The stressed spring assembly 16 is safely retained as a unit in its spring stressed condition by the safety assembly 18. As shown, safety assembly 18 includes a cap element 90 adapted to fit over the rear end portion of the housing member 88 and an integral safety pin element 92 which extends forwardly from the interior surface of the end wall portion of the cap element 90 in coextensive relation with the skirt portion thereof. Safety pin element 92 extends forwardly through the apertured locking ring 78 between the spring fingers 76 when the cap element 90 is engaged on the end of the housing member 88 so as to prevent the spring fingers from being cammed inwardly.

The housing member 88 is arranged to be inserted as an assembled component of the stressed spring and manual safety assemblies 16 and 18 within the rearward end portion of the outer housing member 20 and to be stationarily held therein. To this end, the outer housing member 20 has an annular groove 94 formed in the rear end portion of the interior periphery thereof. Housing member 88 is formed with an integral cooperating annular projection or flange 96 shaped to snap-fit within the annular groove 94. When flange 96 is engaged within groove 94, the barbs 66 on the forward end of collet member 62 engage within the rearward end of spacer 60 so that the stressed spring assembly 16 as a unit is held in cooperating relation with the injecting assembly 14 to effect actuation thereof in response to the operator performing the actuating procedure of removing the safety assembly 18, gripping the outer housing member 20 and moving it forwardly until the forward end 24 of the housing member 22 engages the patient to arrest its forward movement and enable the continued forward movement of the housing member 20 and housing member 88 fixed thereto to move the cam release surface 84 into engagement with cam surfaces 82. The resultant inward movement of spring fingers 76 disengages locking surfaces 80 from the locking ring 78 and thus releases the stressed spring 68. The spring force thus released is applied to plunger 50 and transmitted by the liquid dosage 54 to the container 48 which moves forwardly within housing member 22 causing needle 56 to extend through sheath 58 and into the muscle tissue of the patient until its forward movement is arrested by the compression of the rubber sheath 58 between the container 48 and housing member 22. After the forward movement of the needle 56 and container 48 is arrested, the continued forward movement of the plunger 50 under the influence of the released spring force causes the liquid medicament dosage 54 to burst the sealing diaphragm and to be moved into the muscle tissue of the patient through the needle.

In accordance with the principles of the present invention in order to protect the glass container 48 from breakage due to injector assembly droppage or unwanted contact by the collet member 62 and/or spring 68 during actuation, there is provided a glass protecting sleeve structure, generally indicated at 98. As shown, the sleeve structure 98 includes a cylindrical portion 100 and a flange portion 102 extending radially outwardly from one end of the cylindrical portion 100. The sleeve structure 98 may be formed of any suitable material, a preferred material being thermoplastic resin, preferably polyethylene. While the sleeve structure 98 may be formed by any desired procedure, the preferred method of formation is by injection molding. Where the preferred method of forming the sleeve structure 98 is utilized, the cylindrical portion 100 will be formed with a slight taper sufficient to enable the structure to be readily removed from the molding die. For purposes of clear illustration, the cylindrical portion 100 is shown in the drawings with an exaggerated thickness and no taper. A typical maximum wall thickness of the cylindrical portion 100 is approximately 0.016". A typical thickness for the flange portion is 0.020".

It will be noted that the exterior peripheral size of the cylindrical portion 100 is such as to enable the cylindrical portion 100 to engage within the rear end portion of the glass container 48, which, when the protective sleeve structure 98 is utilized, is preferably untempered with respect to heat tempering. The glass may be chemically tempered if desired. The interior periphery of the glass container is substantially the same or slightly larger than the cylindrical portion 100. The interior peripheral dimension of the cylindrical portion 100 is such as to receive therein the exterior periphery of the spacer 60. As best shown in FIG. 4, the spacer 60 may include peripheral ribs 104 which are sized to engage within the interior of the cylindrical portion 100. The cylindrical portion 100 has an axial extent sufficient to engage within substantially the entire rearward end portion of the container 48 disposed rearwardly of the plunger 50. As best shown in FIG. 3, the flange portion 102 extends radially outwardly from the rearward end of the cylindrical portion 100 so as to overlie a rearward end edge 106 of the container 48 and an adjacent contiguous rearward edge 108 of the housing member 22. The exterior diameter of the flange portion 102 is of a size to center within the interior periphery of the outer housing member 20.

As best shown in FIGS. 1 and 3, when the injector 10 is disposed in its inoperative storage position, the sleeve structure 98 serves as a protective buffer between the forward shoulders 64 of the collet member 62 and the adjacent rearward extremity of the glass container 48 as well as a protective buffer between the forward volute of the stressed spring 68 and the rearward edge 106 of the glass container. The flange 102 also serves as a buffer between the forward flange 74 of the member 72 and the rearward edge 106 of the glass container 48. This protective buffer provided by the sleeve structure 98 materially aids in preventing breakage of the glass container due to droppage where contact of the buffered elements could otherwise take place with the rear end portion and rear edge 106 of the glass container 48.

FIG. 2 illustrates the manner in which the sleeve structure 98 provides a guiding and protecting function for the glass container 48 during the operation of the automatic injector 10. Normal operation of the injector 10 is initiated, as aforesaid, by removing the safety cap structure 18. Thereafter, the user grasps the exterior periphery of the outer housing member 20 and moves the entire injector 10 toward an appropriate muscle tissue such as the thigh. When the forward end 24 of the inner housing member 22 engages the thigh, the outer housing member 20 continues to move forwardly, causing the frustoconical surface 84 of the member 88 to slide with respect to the cam surface 82, thus moving the spring fingers inwardly and disengaging the locking surfaces 80 from the locking ring 78. Upon disengagement of the locking surfaces 80 with the locking ring 78, stressed spring 68 is released which moves the member 72 rearwardly and the collet member 62 forwardly. As previously indicated, the forward movement of the collet member 62 results in a forward movement of the container 48. It will be noted that as the rear edge 106 of the container 48 leaves its contiguous position of alignment with the rear edge 108 of the interior housing member 22, the latter serves to retain the sleeve structure 98 against forward movement with the glass container 48. Thus, the initial forward movement of the collet member 62 under the action of the stressed spring 68, as well as the initial movement of the forward volutes of the spring itself takes place within the interior surface of the sleeve structure 98. The sleeve structure consequently provides a centering action for the collet member and spring which materially aids in preventing contact between the collet and/or with the glass container 48. In addition, the exterior periphery of the cylindrical portion 100 of the sleeve structure 98, serves to center and guide the initial movement of the container.

As previously indicated, the forward movement of the container 48 is arrested by the compression of the rubber sheath 58 and during this forward movement, hypodermic needle 56 extends forwardly through the end of the sheath 58 and into the muscle tissue of the user. As soon as the forward movement of the container is arrested, the continued movement of the plunger 50 serves to effect the discharge of the liquid medicament dosage 54 outwardly of the container 48 through the needle 56 and into the muscle tissue of the user. FIG. 2 illustrates that the sleeve structure 98 continues to have a centering action on the volutes of the spring 68 as the collet member 62 passes therethrough.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. In an automatic injector of the type including a housing having a glass container therein, a hypodermic needle connected with the forward end of said glass container, the rearward end portion of said glass container being defined by a generally cylindrical interior periphery, a generally cylindrical exterior periphery and an annular rear end edge between the rearward ends of said cylindrical peripheries, a plunger slidably sealingly mounted within the interior periphery of said container, a dosage of liquid medicament within said container forwardly of said plunger and a stressed spring actuating assembly releasable to transmit an axial force to said plunger to move the same forwardly so as to correspondingly move the glass container within said housing into a limiting position wherein said needle is extended into the muscle tissue of a patient and thereafter to move said plunger within said glass container to discharge the medicament dosage therein through said needle and into the patient, the improvement which comprises a glass container protecting sleeve of thin plastic material assembled in an operative position within said housing with respect to said glass container when said stressed spring actuating assembly is in an unreleased condition so as to protect the glass container against fracture (1) due to handling impacts prior to release of said stressed spring assembly and (2) due to the force transmitted to said plunger following the release of said stressed assembly, said sleeve including a cylindrical portion disposed in engagement with a cylindrical periphery of said glass container when said protective sleeve is in said operative position and an annular flange extending from the rear end of said cylindrical portion disposed in rearwardly adjacent relation to the rear end edge of said glass container when said protective sleeve is in said operative position.

2. The improvement as defined in claim 1 wherein said plunger is slidably sealingly mounted within the interior periphery of said container at a position forwardly of the rear end edge thereof when said stressed spring actuating assembly is in said unreleased condition, the cylindrical portion of said sleeve extending forwardly from the inner periphery of said annular flange in engagement with the portion of the cylindrical interior periphery of said container extending from the rear end edge thereof to the position forwardly therefrom within which said plunger is mounted.

3. The improvement as defined in claim 2 wherein said housing includes a fixed outer tubular member and a rearwardly movable inner tubular member including a rear end edge normally disposed in contiguous surrounding relation with the rear end edge of said container, said sleeve flange extending radially outwardly beyond the rear end edge of said container in rearwardly adjacent relation to the rear end edge of said inner tubular housing member so as to be held against forward movement by engagement therewith so that the cylindrical portion thereof will act as a centering stationary guide for said stressed spring assembly when the latter is released to move said plunger as aforesaid.

4. The improvement as defined in claim 3 wherein an annular spacer member is connected with said plunger and disposed within the cylindrical portion of said sleeve extending rearwardly from said plunger within the cylindrical interior periphery of said container.

5. The improvement as defined in claim 3 wherein said glass container is untempered with respect to heat tempering.

6. The improvement as defined in claim 1 wherein said glass container is untempered with respect to heat tempering.

* * * * *